(12) United States Patent
Bhattacharyya et al.

(10) Patent No.: US 9,079,846 B2
(45) Date of Patent: *Jul. 14, 2015

(54) PROCESS FOR OXIDIZING IMPURITIES IN CRUDE TEREPHTHALIC ACID

(71) Applicants: UOP LLC, Des Plaines, IL (US); Boreskov Institute of Catalysis, Novosibirsk (RU)

(72) Inventors: Alakananda Bhattacharyya, Glen Ellyn, IL (US); Nina Kuznetsova, Novosibirsk (RU); Bair S. Bal'zhinimaev, Novosibirsk (RU)

(73) Assignees: UOP LLC, Des Plaines, IL (US); BORESKOV INSTITUTE OF CATALYSIS SIBERIAN BRANCH OF THE RUSSIAN ACADEMY OF SCIENCES, Novosibirsk (RU)

( * ) Notice: Subject to any disclaimer, the term of this patent is extended or adjusted under 35 U.S.C. 154(b) by 264 days.

This patent is subject to a terminal disclaimer.

(21) Appl. No.: 13/650,731

(22) Filed: Oct. 12, 2012

(65) Prior Publication Data

US 2014/0107375 A1 Apr. 17, 2014

(51) Int. Cl.
*C07C 51/42* (2006.01)
*C07C 51/487* (2006.01)

(52) U.S. Cl.
CPC ............... *C07C 51/42* (2013.01); *C07C 51/487* (2013.01)

(58) Field of Classification Search
CPC ...................................................... C07C 51/42
USPC ........................................................... 562/485
See application file for complete search history.

(56) References Cited

U.S. PATENT DOCUMENTS

| | | | |
|---|---|---|---|
| 3,654,351 | A | 4/1972 | Witt |
| 2009/0326265 | A1* | 12/2009 | Hashmi et al. ............... 562/416 |
| 2010/0174111 | A1 | 7/2010 | Rogers et al. |
| 2011/0105770 | A1 | 5/2011 | Liu et al. |
| 2012/0004448 | A1 | 1/2012 | Bhattacharyya et al. |
| 2012/0004451 | A1 | 1/2012 | Bhattacharyya et al. |
| 2012/0004456 | A1 | 1/2012 | Bhattacharyya |

FOREIGN PATENT DOCUMENTS

| | | |
|---|---|---|
| CN | 101407445 A | 4/2009 |
| GB | 1465664 A | 2/1977 |

OTHER PUBLICATIONS

PCT Search Report dated Jan. 30, 2014 for PCT/US2013/063972.

* cited by examiner

*Primary Examiner* — Yevegeny Valenrod

(57) ABSTRACT

A process for oxidizing solid crude terephthalic acid is described. The process includes contacting solid crude terephthalic acid with a solvent comprising a carboxylic acid and one or more of an ionic liquid or ammonium acetate; a bromine source; a catalyst; and an oxidizing agent to produce solid purified terephthalic acid at a temperature of about 100 to about 210° C., and a pressure of about 2 to about 4.5 MPa, for a time of about 5 to about 60 min, and recovering the solid purified terephthalic acid.

20 Claims, 1 Drawing Sheet

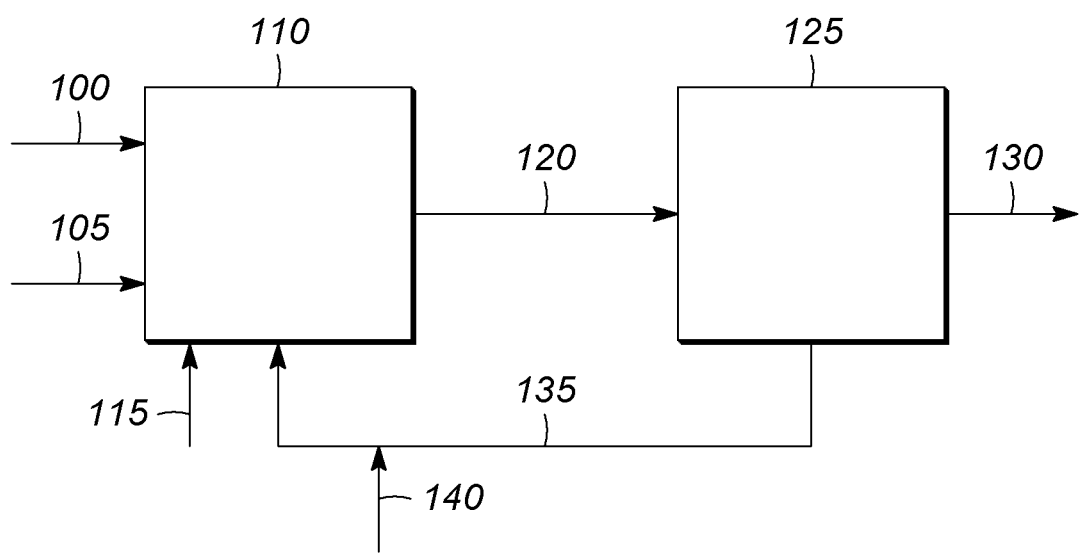

PROCESS FOR OXIDIZING IMPURITIES IN CRUDE TEREPHTHALIC ACID

FIELD OF THE INVENTION

This invention relates to processes for oxidizing alkyl-aromatic compounds. More particularly, the invention relates to processes for oxidizing solid, crude terephthalic acid.

BACKGROUND OF THE INVENTION

Oxidation of alkyl aromatic compounds, e.g., toluene and xylenes, are important commercial processes. A variety of oxidation products may be obtained including aromatic carboxylic acids such as terephthalic acid (1,4-benzenedicarboxylic acid) and isophthalic acid (1,3-benzenedicarboxylic acid) which are used, for example, in the polymer industry.

It is known that oxidation products, such as aromatic alcohols, aromatic aldehydes, aromatic ketones, and aromatic carboxylic acids, may solidify or crystallize at oxidation conditions and/or as the reaction mixture cools. Thus, mixtures of oxidation products may be produced which require further processing to increase the purity of the desired product. For example, in the production of terephthalic acid, the oxidation product is often referred to as crude terephthalic acid because it contains impurities including color bodies and intermediate oxidation products, especially 4-carboxybenzaldehyde (4-CBA). To obtain polymer grade or purified terephthalic acid, various purification steps are known in the art including: washing the crude terephthalic acid with water and/or a solvent, additional oxidation or crystallization steps, and reacting a solution of dissolved crude terephthalic acid with hydrogen at hydrogenation conditions usually including a catalyst comprising palladium and carbon. Often several purification steps are used.

U.S. Pat. No. 2,833,816 discloses processes for oxidizing aromatic compounds to the corresponding aromatic carboxylic acids. A process for the liquid phase oxidation of alkyl aromatic compounds uses molecular oxygen, a metal or metal ions, and bromine or bromide ions in the presence of an acid. The metals may include cobalt and/or manganese. Exemplary acids are lower aliphatic mono carboxylic acids containing 1 to 8 carbon atoms, especially acetic acid.

U.S. Pat. No. 6,355,835 discloses a process for the preparation of benzene dicarboxylic acids by liquid phase oxidation of xylene isomers using oxygen or air by oxidizing in the presence of acetic acid as a solvent, a cobalt salt as a catalyst, and an initiator. The oxidation step is followed by flashing the reaction mixture to remove volatile substances and cooling and filtering the material to get crude benzene di-carboxylic acid as a solid product and a filtrate. Recrystallizing the crude benzene di-carboxylic acid to obtain at least 99% purity and recycling of the filtrate are also disclosed.

U.S. Pat. No. 7,094,925 discloses a process for preparing an alkyl-aromatic compound. The process includes mixing an oxidizing agent or sulfur compound in the presence of an ionic liquid. Air, dioxygen, peroxide, superoxide, or any other form of active oxygen, nitrite, nitrate, and nitric acid or other oxides or oxyhalides of nitrogen (hydrate or anhydrous) can be used as the oxidizing agent. The process is typically carried out under Bronstead acidic conditions. The oxidation is preferably performed in an ionic liquid containing an acid promoter, such as methanesulfonic acid. The product is preferably a carboxylic acid or ketone or intermediate compound in the oxidation, such as an aldehyde, or alcohol.

U.S. Pat. No. 7,985,875 describes a process for preparing an aromatic polycarboxylic acid by liquid phase oxidation of a di- or tri-substituted benzene or naphthalene compound. The process involves contacting the aromatic compound with an oxidant in the presence of a carboxylic acid solvent, a metal catalyst, and a promoter in a reaction zone. The promoter is an ionic liquid comprising an organic cation and a bromide or iodide anion. The promoter is used in a concentration range of about 10 to about 50,000 ppm (based on solvent) with a preferred range of 10-1,000 ppm. No other promoters, such as bromine-containing compounds, need to be used in the process. The process produces crude terephthalic acid (CTA) having 1.4-2.2% 4-CBA. Purification of the CTA is required to obtain purified terephthalic acid (PTA).

US 2010/0174111 describes a process for purifying aryl carboxylic acids, such as terephthalic acid. The impure acid is dissolved or dispersed in an ionic liquid. A non-solvent (defined as a molecular solvent for which the ionic solvent has high solubility and for which the aryl carboxylic acid has little or no solubility) is added to the solution to precipitate the purified acid.

U.S. Pat. No. 7,692,036, 2007/0155985, 2007/0208193, and 2010/0200804 disclose a process and apparatus for carrying out the liquid-phase oxidation of an oxidizable compound. The liquid phase oxidation is carried out in a bubble column reactor that provides for a highly efficient reaction at relatively low temperatures. When the oxidized compound is para-xylene, the product from the oxidation reaction is CTA which must be purified. Purification is said to be easier than for conventional high temperature processes.

There is a need for a method of purifying solid crude terephthalic acid.

SUMMARY OF THE INVENTION

One aspect of the present invention is a process for oxidizing solid crude terephthalic acid. In one embodiment, the process includes contacting solid crude terephthalic acid with a solvent comprising a carboxylic acid and one or more of an ionic liquid or ammonium acetate; a bromine source; a catalyst; and an oxidizing agent to produce solid purified terephthalic acid at a temperature of about 100 to about 210° C., and a pressure of about 2 to about 4.5 MPa, for a time of about 5 to about 60 min; and recovering the solid purified terephthalic acid.

BRIEF DESCRIPTION OF THE DRAWING

The FIGURE is a general process flow diagram for one embodiment of a process for producing purified oxidized terephthalic acid.

DETAILED DESCRIPTION OF THE INVENTION

The present invention provides a solution to the problem of purifying solid crude terephthalic acid. The solid crude terephthalic acid is oxidized in an ionic liquid and/or ammonium acetate solvent, eliminating the elaborate and expensive hydrogenation process previously used to reduce 4-CBA and color bodies in solid crude terephthalic acid.

The process includes contacting solid crude terephthalic acid with a solvent comprising a carboxylic acid and one or more of an ionic liquid or ammonium acetate; a bromine source; a catalyst; and an oxidizing agent to produce purified terephthalic acid at a temperature of about 100 to about 210° C., and a pressure of about 2 to about 4.5 MPa, for a time of about 5 to about 60 min.

The contacting step(s) may be practiced in laboratory scale experiments through full scale commercial operations. The process may be operated in batch, continuous, or semi-continuous mode. The contacting step can take place in various ways. The order of addition of the components (e.g. crude terephthalic acid, solvent, bromine source, catalyst, and oxidizing agent) is not critical. For example, the components can be added individually, or two or more components may be combined or mixed before being combined or mixed with other components.

The crude terephthalic acid can be made by any type of process. For example, any of the commercially available processes discussed in the patents cited above or elsewhere can be used, if desired. The crude terephthalic acid (however produced) is crystallized to a solid.

The solid crude terephthalic acid 100 enters a reaction zone 110 where it is contacted with a solvent 105 comprising a carboxylic acid and one or more of an ionic liquid or ammonium acetate; a bromine source; a catalyst; and an oxidizing agent 115. The reaction zone 110 is operated at a temperature of about 100 to about 210° C., and a pressure of about 2 to about 4.5 MPa, for a time of about 5 to about 60 min.

After contacting the crude terephthalic acid with the solvent, bromine source, catalyst, and oxidizing agent, the effluent 120 from the reaction zone 110 can be crystallized. Crystallization can involve one or more post reaction zones and/or one or more crystallizers 125. If a post reaction zone is needed to increase conversion further, additional oxidizing agent will be required. The post reaction zones/crystallizers 125 can operate at lower pressure and lower temperature to help with crystallization. One or more crystallizers are used to complete the crystallization of the terephthalic acid at lower temperatures. The solvent comprises the carboxylic acid and one or more of the ionic liquid and/or ammonium acetate. The solvent provides a medium where the impurities and/or intermediates remain or are further oxidized to terephthalic acid, thereby substantially reducing the impurities.

The crystallized product 130 is separated from the solvent, washed, dried, and stored. The product can be crystallized using one or more of crystallizers, filters, centrifuges, and dryers, as is known in the art. The product crystals can be washed with solvent in a separator zone. The purified product is dried and stored in the product silo. Additional separation devices may be needed to ensure that the product meets the product specification before storage.

The mother liquor 135 can be recycled back to the reaction zone if desired. Make-up solvent 140 can be added as needed.

The solvent includes a carboxylic acid. The amount of carboxylic acid is decreased compared with conventional processes in order to avoid excessive solvent volumes. The carboxylic acid is present in an amount of about 30 to about 70 wt %. The carboxylic acid desirably has from 1 to 7 carbon atoms. In an embodiment, the carboxylic acid comprises acetic acid. The solvent may contain more than one carboxylic acid. For example, the solvent may further comprise benzoic acid. In another embodiment, the carboxylic acid of the solvent is acetic acid.

The solvent includes one or more ionic liquid(s), ammonium acetate, or both. The ammonium acetate can be present in an amount of 0 to about 30 wt %. There can be one or more ionic liquids present in an amount of 0 to about 30 wt %.

Generally, ionic liquids are non-aqueous, organic salts composed of ions where the positive ion is charge balanced with a negative ion. These materials have low melting points, often below 100° C., undetectable vapor pressure, and good chemical and thermal stability. The cationic charge of the salt is localized over hetero atoms, and the anions may be any inorganic, organic, or organometallic species.

Most ionic liquids are formed from cations that do not contain acidic protons. The synthesis of ionic liquids can generally be split into two parts: formation of the desired cation, and anion exchange to form the desired product. Quaternization of an amine or phosphine, for example, is the initial step in the synthesis of the cation of an ionic liquid. If it is not possible to form the desired anion directly by the quaternization reaction, a further step is required.

There are estimated to be hundreds of thousands of simple ion combinations to make ionic liquids, and an almost endless ($10^{18}$) number of potential ionic liquid mixtures. This implies that it should be possible to design an ionic liquid with the desired properties to suit a particular application by selecting anions, cations, and mixture concentrations. Ionic liquids can be adjusted or tuned to provide a specific melting point, viscosity, density, hydrophobicity, miscibility, etc. for specific applications. The thermodynamics and reaction kinetics of processes carried out in ionic liquids are different from those in conventional media. This creates new opportunities for catalytic reactions, separations, extractions, combined reaction/separation processes, heat transfer agents, hydraulic fluids, paint additives, electrochemistry applications, as well as many others. Ionic liquids do not emit volatile organic compounds (VOCs), providing a basis for clean manufacturing, e.g., "green chemistry."

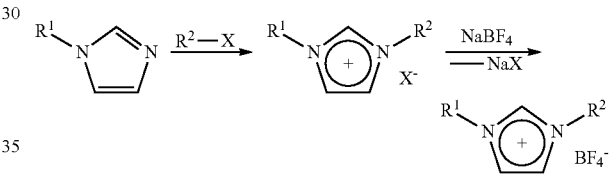

$R^1$ = methyl, vinyl, allyl
$R^2$ = ethyl, propyl, butyl, isobutyl, propargyl, allyl, crotyl, methallyl
X = Cl, Br Cations and anions for ionic liquids are described in US Publication 2010/0174111, for example.

The organic cation can comprise a linear, branched, or cyclic heteroalkyl unit. The term "heteroalkyl" refers to a cation comprising one or more heteroatoms chosen from nitrogen, oxygen, sulfur, boron, arsenic, antimony, aluminum, or phosphorous capable of forming a cation. The heteroatom can be a part of a ring formed with one or more other heteroatoms, for example, pyridinyl, imidazolinyl rings, that can have substituted or unsubstituted linear or branched alkyl units attached thereto. In addition, the cation can be a single heteroatom wherein a sufficient number of substituted or unsubstituted linear or branched alkyl units are attached to the heteroatom such that a cation is formed.

Non-limiting examples of heterocyclic and heteroaryl units that can be alkylated to form cationic units include imidazole, pyrazoles, thiazoles, isothiazoles, azathiozoles, oxothiazoles, oxazines, oxazolines, oxazaboroles, dithiozoles, triazoles, selenozoles, oxaphospholes, pyrroles, boroles, furans, thiphenes, phospholes, pentazoles, indoles, indolines, oxazoles, isothirazoles, tetrazoles, benzofuran, dibenzofurans, benzothiophenes, dibenzothoiphenes, thiadiazoles, pyrdines, pyrimidines, pyrazines, pyridazines, piperazines, piperidines, morpholines, pyrans, annolines, phthalazines, quinazolines, quinoxalines, alkyl phosphonium, and combinations thereof.

The anionic portion of the ionic liquid can comprise an inorganic, organic, or organometallic moiety. Non-limiting examples of anions include inorganic anions: halides, (e.g., F, Cl, Br, and I); borides, $BX_4$, wherein X represents halogen, (e.g., $BF_4$, $BCl_4$), and the like; phosphates(V), $PX_6$; $PF_6$, and the like; arsenate(V), $AsX_6$; $AsF_6$, and the like; stibate(V) (antimony), $SbX_6$; $SbF_6$, and the like; tosylates; imides; $CO_3^{2-}$; $NO_2^{1-}$, $NO_3^{1-}$, $SO_4^{2-}$, $PO_4^{3-}$, $(CF_3)SO_3^{1-}$.

Other non-limiting examples of ionic liquid anions include substituted azolates, that is, five membered heterocyclic aromatic rings that have nitrogen atoms in either positions 1 and 3 (imidazolates); 1, 2, and 3 (1,2,3-triazolates); or 1, 2, 4 (1,2,4-triazolate). Substitutions to the ring occur at positions that are not located in nitrogen positions (these are carbon positions) and include CN (cyano-), $NO_2$ (nitro-), and $NH_2$ (amino) group appended to the heterocyclic azolate core.

Further non-limiting examples of anions include substituted or unsubstituted borides: $B(R^{10})_4$; substituted or unsubstituted sulfates: $(RO)S(=O)_2O$; substituted or unsubstituted acyl units $RCO_2$, for example, acetate $CH_3CO_2$, proprionate, $CH_3CH_2CO_2$, butyrate $CH_3CH_2CH_2CO_2$, and benzylate, $C_6H_5CO_2$; substituted or unsubstituted phosphates: $(RO)_2P(=O)O$; substituted or unsubstituted carboxylates: $(RO)C(=O)O$; substituted or unsubstituted azolates wherein the azolate can be substituted on a carbon atom by a unit chosen from cyano, nitro, and amino. R can be an organic, inorganic, or organometallic group. Non-limiting examples of R include hydrogen; substituted or unsubstituted linear branched, and cyclic alkyl; substituted or unsubstituted linear, branched, and cyclic alkoxy; substituted or unsubstituted aryl; substituted or unsubstituted aryloxy; substituted or unsubstituted heterocyclic; substituted or unsubstituted heteroaryl; acyl; silyl; boryl; phosphino; amino; thio; and seleno.

In an embodiment, ionic liquids suitable for use include, but are not limited to, one or more of imidazolium ionic liquids, pyridinium ionic liquids, tetra alkyl ammonium ionic liquids, and phosphonium ionic liquids. More than one ionic liquid may be used. Imidazolium, pyridinium, and ammonium ionic liquids have a cation comprising at least one nitrogen atom. Phosphonium ionic liquids have a cation comprising at least one phosphorus atom. In an embodiment, the ionic liquid comprises a cation selected from alkyl imidazolium, di-alkyl imidazolium, and combinations thereof. In another embodiment, the ionic liquid comprises an anion selected from halides, acetate, carboxylates, and combinations thereof. The ionic liquid may comprise at least one of 1-butyl 3-methyl imidazolium acetate (BMImOAc), 1-butyl 3-methyl imidazolium bromide (BMImBr), 1-hexyl 3-methyl imidazolium acetate, and 1-hexyl 3-methyl imidazolium bromide.

The ionic liquid can be provided, or it can be generated in situ from appropriate precursors, or both. If it is generated in situ, the solvent comprises precursors of one or more ionic liquids. The ionic liquid precursors comprise a cation precursor, such as an alkyl imidazole, alkyl pyridine, alkyl amine, alkyl phosphine, and the like, and an anion precursor, such as alkyl or aryl halides or acetates. In an embodiment, the precursors are methyl imidazole and butyl bromide.

The mode of introducing the ionic liquid precursors may vary depending on the nature and purity of the product desired. In one mode of addition, the cation precursors and the anion precursors (generally liquids at room temperature and pressure) are mixed with a carboxylic acid (for example, acetic acid) solvent and introduced into the oxidation reactor(s). In another mode of addition, the ionic liquid precursors may be mixed with the crude terephthalic acid and introduced into the oxidation reactors. In another mode of addition, both cation and anion ionic liquid precursor components may be introduced into the bottom of the reactor without pre-mixing with any other oxidation reactor components such as the feed, carboxylic acid solvent, and catalyst package.

In an embodiment, the solvent has a ratio of the carboxylic acid to the ionic liquid within a range of about 1 to 12 by weight. In an embodiment, the solvent contains more than 5% by wt ionic liquid or ammonium acetate or both. The amount of ionic liquid includes ionic liquid precursors, if present.

Optionally, water may be present in the mixture. The water may be added to the mixture or generated in the mixture during the oxidation process. In an embodiment, the amount of water ranges from about 0.1 wt % to about 20 wt %, relative to the total oxidation reaction mixture.

The catalyst comprises at least one of cobalt, manganese, titanium, chromium, copper, nickel, vanadium, iron, molybdenum, tin, cerium and zirconium. In an embodiment, the catalyst comprises cobalt and manganese. The metal may be in the form of an inorganic or organic salt. For example, the metal catalyst may be in the form of a carboxylic acid salt, such as, a metal acetate and hydrates thereof. Exemplary catalysts include cobalt (II) acetate tetrahydrate and manganese (II) acetate, individually or in combination. In an embodiment, the amount of manganese (II) acetate is less than the amount of cobalt (II) acetate tetrahydrate by weight.

The amount of catalyst used in the invention may vary widely. For example, the amount of cobalt may range from about 0.001 wt % to about 2 wt % relative to the weight of the solvent. In an embodiment, the amount of cobalt ranges from about 0.05 wt % to about 2 wt % relative to the weight of the solvent. The amount of manganese may range from about 0.001 wt % to about 2 wt % relative to the weight of the solvent. In an embodiment, the amount of manganese ranges from about 0.05 wt % to about 2 wt % relative to the weight of the oxidation mixture. In another embodiment, the ratio of cobalt to manganese ranges from about 3:1 to about 1:2 by weight on an elemental metal basis.

Bromine sources are generally recognized in the art as being catalyst promoters and include bromine, ionic bromine, e.g. HBr, NaBr, KBr, $NH_4Br$; and/or organic bromides which are known to provide bromide ions at the oxidation conditions, such as, benzylbromide, mono and di-bromoacetic acid, bromoacetyl bromide, tetrabromoethane, ethylene dibromide. In an embodiment, the bromine source comprises or consists essentially of or consists of hydrogen bromide. The amount of hydrogen bromide may range from about 0.01 wt % to about 5 wt %, relative to the weight of the solvent. In another embodiment, the amount of hydrogen bromide ranges from about 0.05 wt % to about 2 wt %, relative to the weight of the oxidation mixture.

Suitable oxidizing agents for the process provide a source of oxygen atoms to oxidize the 4-CBA, and/or another intermediate oxidization product at the oxidation conditions employed. Examples of oxidizing agents include peroxides, superoxides, and nitrogen compounds containing oxygen such as nitric acids. In an embodiment, the oxidizing agent is a gas comprising oxygen, e.g. air, carbon dioxide, and molecular oxygen. The gas may be a mixture of gasses. The amount of oxygen used in the process is preferably in excess of the stoichiometric amount required for the desired oxidation process. In an embodiment, the amount of oxygen contacted with the mixture ranges from about 1.2 times the stoichiometric amount to about 100 times the stoichiometric amount. Optionally, the amount of oxygen contacted with the mixture may range from about 2 times the stoichiometric amount to about 30 times the stoichiometric amount.

At least a portion of the components provides a liquid phase, although dissolution of one or more of the mixture components may not be complete at any or some time during the process. The liquid phase may be formed by mixing the components at ambient conditions. In another embodiment, the liquid phase is formed as the temperature of the mixture increases to the oxidation temperature. A mixture of the components may be formed prior to the oxidation step, in the same or different vessel as that used in the oxidation step. In another embodiment, a mixture of the components is formed in an oxidation reactor, e.g. adding various streams of the components individually and/or in combination to a continuous or semi-continuous oxidation reactor. The combined components, and/or various streams of the components may be heated before they are mixed together.

Though many conventional alkyl aromatic oxidation processes are typically conducted in a mixed phase, and often include three phases (e.g. solid, gas, and liquid), they are frequently referred to in the art as "liquid phase" oxidation processes because the oxidation conditions are maintained to provide at least a portion of the mixture in the liquid phase. It is also known in the art that the number of phases present may vary over time during the process. Processes according to the instant invention may also be conducted in a liquid phase or mixed phase in a similar manner as known in the art.

Conventional, liquid phase oxidation reactors as known in the art may be used to practice the invention. Examples include vessels, which may have one or more mechanical agitators, and various bubble column reactors such as those described in U.S. Pat. No. 7,692,036. It is also known to design, operate, and control such reactors and the oxidation reaction for the oxidation conditions employed including, e.g., the temperature, pressure, liquid and gas volumes, and corrosive nature of the liquid and gas phases where applicable. See, e.g. U.S. Pat. No. 7,692,036 and U.S. Pat. No. 6,137,001.

The contacting step generally takes at a temperature ranging from about 100° C. to about 210° C., or about 150 to about 200° C. The pressure generally ranges from about 2 to about 4.5 MPa or about 4.0 to about 4.1 MPa. The residence time generally ranges from about 5 to about 60 min, or about 5 to about 45 min. That is, the mixture has a temperature and a pressure within these ranges and may be maintained within these ranges for a period of time within the residence time range. The temperature, pressure and residence time may vary based on a variety of factors including for example, the reactor configuration, size, and whether the process is, batch, continuous, or semi-continuous. One condition may also vary based on other conditions. For example, use of a particular temperature range may enable use of a different residence time range.

In an embodiment, the purified terephthalic acid produced by the instant invention may precipitate, crystallize, or solidify in a liquid phase mixture at the oxidation conditions and/or as the mixture cools. Thus, a mixture according to the invention may further comprise solid terephthalic acid.

If any terephthalic acid amide is formed in the oxidation step, it will be hydrolyzed to pure terephthalic acid in the crystallization step.

Processes according to the invention may comprise one or more additional contacting steps. In an embodiment, a second contacting step includes a second temperature that is lower than the temperature of the first contacting step. Processes according to the invention may include additional contacting steps of the invention as described herein, and/or the invention may be combined with other oxidizing steps such as conventional oxidizing steps known in the art. Multiple contacting and/or oxidation steps may be conducted in series and/or parallel and may be combined with other process steps such as purification steps described herein.

In another embodiment, the invention further comprises purifying the oxidation product. Purifying may comprise one or more additional steps to isolate and purify the oxidation product. Examples of purifying steps include: separating wherein the purified terephthalic acid is separated from the mother liquor or another liquid phase such as by filtration and/or centrifugation; washing wherein the oxidation product is washed, for example with water and/or another solvent component; and drying the oxidation product. Such additional processing steps have been described in the general literature and are well known to those of ordinary skill in the art to be used in various combinations to purify oxidation products of the invention. See for example, the references cited in this application and the art cited therein.

A purification step of the instant invention may further comprise one or more solvent contacting steps. A solvent contacting step comprises contacting the purified terephthalic acid, also including washed or dried purified terephthalic acid, with a third solvent comprising at least one of water, a carboxylic acid, an ionic liquid, and a mother liquor to produce a purified oxidation product. In an embodiment, the solvent of the solvent contacting step contains ionic liquid and carboxylic acid, and optionally mother liquor. The composition of the solvent for the solvent contacting step can be as described above for the contacting step.

Solvent contacting may leach impurities from the solid purified terephthalic acid, and/or the oxidation product may be partially or completely dissolved in the solvent. Solvent contacting conditions include a solvent contacting temperature. The solvent contacting temperature may be lower than the oxidation temperature. In an embodiment, the solvent contacting temperature is at least 20° C. lower than the oxidation temperature. Solvent contacting may be practiced for example in the one or more crystallizers that follow the oxidation reactor in some conventional processes. The oxidation product may solidify, precipitate, or crystallize in the solvent of the solvent contacting step.

The product made by the process, either initially or following one or more additional oxidizing and/or purification steps, can contain less than about 2500 ppm 4-CBA, or less than about 2000 ppm 4-CBA, or less than about 1500 ppm 4-CBA, or less than about 1000 ppm 4-CBA, or less than about 750 ppm 4-CBA, or less than about 500 ppm 4-CBA, or less than about 250 ppm 4-CBA, or less than about 100 ppm 4-CBA, or less than about 50 ppm 4-CBA, or less than about 25 ppm 4-CBA.

Example 1

Oxidative Purification of Crude Terephthalic Acid in the Presence of $NH_4OAc$

The oxidative purification of crude terephthalic acid industrial product from 4-CBA was evaluated. The oxidative treatment of the crude terephthalic acid in the presence of $NH_4OAc$ resulted in oxidation of 4-CBA. The oxidation was performed under the following conditions: 210° C., and 4.6 MPa (45 atm) of air pressure. The composition of the reaction mixture was 18 g $NH_4OAc$ and 15 g of crude terephthalic acid in 30 g acetic acid, 0.4 g $Co(OAc)_2$ $4H_2O$, 0.3 g $Mn(OAc)_2$ $4H_2O$, and 0.4 g HBr. The crude terephthalic acid contained 3600 ppm 4-CBA and some other impurities. The results of the oxidation runs are represented in Table 1.

TABLE 1

| Run No. | Purification | Impurities, ppm | | |
|---|---|---|---|---|
| | | 4-CBA | BA | TolA |
| Crude TA | no | 3600 | 400 | 458 |
| 10.03 | 210° C., 0.5 h without air (re-crystallization) | 1192 | — | — |
| 11.03-2 | 210° C., 40 atm, 0.5 h | — | 457 | — |
| 11.03-1 | 210° C., 40 atm, 1 h | — | 2246 | — |

The 4-CBA was completely removed after oxidative treatment in the presence of $NH_4OAc$. However, the treatment resulted in a loss of terephthalic acid and the formation of benzoic acid (BA).

Additional testing was performed varying $NH_4OAc$ loading, temperature, and duration of the process under more gentle conditions to remove 4-CBA and to avoid undesirable deep oxidation of the terephthalic acid.

In the following oxidation runs, the reactor was loaded with 30 g acetic acid, 15 g crude terephthalic acid (containing 3600 ppm 4-CBA, 405 ppm BA, and 458 ppm p-toluic acid (p-TolA), $NH_4OAc$ as indicated, 0.4 g $Co(OAc)_2$ $4H_2O$, 0.3 g $Mn(OAc)_2$ $4H_2O$, and 0.4 g HBr (unless indicated otherwise), heated to 200° C., and pressurized with air at 4.1 MPa (40 atm). The mixture was stirred at 1600 rpm for the time specified, and the reactor was cooled to the room temperature. The terephthalic acid precipitate was separated, washed and dried. Results are given in the Table 2.

TABLE 2

| | Conditions | | | Products | | Impurities | | | |
|---|---|---|---|---|---|---|---|---|---|
| | | | | TA | | | | p- | Unknown |
| No. | Additives/g | Temperature/time | grams | TA/area units | amide/area units | 4-CBA/ppm | BA/ppm | TolA/ppm | (retention time 22-23 min) |
| Crude TA | | | | 148363 | | 3600 | 405 | 458 | 254 |
| 24.08 | $NH_4OAc$ 30 g | 200° C., 30 min | 13.8 | 117445 | 27700 | 250 | 453 | 0 | 2410 |
| 26.08 | $NH_4OAc$ 30 g | 200° C., 10 min | 14.1 | 130800 | 16440 | 312 | 280 | 0 | 1670 |
| 30.08 | $NH_4OAc$ 10 g | 200° C., 10 min | 14.2 | 122432 | 21520 | 52 | 146 | 0 | 750 |
| 31.08 | $NH_4OAc$ 6 g | 200° C., 10 min | 14.2 | 117365 | 7678 | 390 | 62 | 0 | 288 |
| 06.09 | $NH_4OAc$ 6 g | 200° C., 10 min | 14.4 | 117868 | 4949 | 680 | 23 | 0 | 142 |
| 07.09 | $NH_4OAc$ 6 g HBr 0.8 g | 200° C., 10 min | n.d. | 117352 | 8230 | 260 | 40 | 0 | 127 |
| 15.09 | $NH_4OAc$ 6 g NH4Br. 0.4 g | 200° C., 10 min | 14.5 | 115658 | 11300 | 188 | 50 | 0 | 270 |

Substantial removal of 4-CBA with minimal formation of BA was achieved in No. 30.08 at 200° C. for 10 min only, in addition to a period of time required to adjust temperature and pressure before and to cool reactor after oxidation. The yield of purified terephthalic acid is 95%. In addition, it was observed that elevation of bromide accelerates oxidation of 4-CBA, while maintaining the same level or even lowering secondary conversion of terephthalic acid to BA.

Example 2

Oxidative Purification of TA in the Presence of BMIMBr

Oxidative purification of the crude terephthalic acid in the presence of 1-butyl 3-methyl imidazolium bromide (BMIMBr) was made in the same conditions. The composition of the mixture was 15 g crude terephthalic acid, 30 g acetic acid, 10 g BMIMBr, 0.4 g $Co(OAc)_2$ $4H_2O$, 0.3 g $Mn(OAc)_2$ $4H_2O$, and 0.4 g HBr.

The results are shown in Table 3.

TABLE 3

| No. | Catalyst/g | Temperature/time | grams | TA/area units | amide/area units | 4-CBA/ppm | BA/ppm | p-TolA/ppm | Unknown (retention time 22-23 min) |
|---|---|---|---|---|---|---|---|---|---|
| Ind | | | | 148363 | | 3600 | 405 | 458 | 254 |
| 20.09 | Co(OAc)$_2$ 0.4 g, Mn(OAc)$_2$ 0.3 g, | 200° C., 30 min | 14.2 | 120771 | 142 | 508 | 33 | 0 | 334 |
| 21.09 | Co(OAc)$_2$ 0.4 g, Mn(OAc)$_2$ 0.3 g, | 200° C., 10 min | 14.6 | 124416 | 69 | 1056 | 21 | 0 | 159 |
| 30.09 | Co(OAc)$_2$ 0.4 g, Mn(OAc)$_2$ 0.3 g, HBr 0.8 g | 200° C., 10 min | | 139796 | 25 | 1106 | 25 | 0 | 121 |
| 03.10 | Co(OAc)$_2$ 0.4 g, Mn(OAc)$_2$ 0.3 g, HBr 0.8 g | 200° C., 30 min | 14.5 | 126045 | 14 | 836 | 9 | 0 | 113 |
| 19.10 | Co(OAc)$_2$ 0.4 g, Mn(OAc)$_2$ 0.3 g, HBr 0.8 g | 200° C., 30 min 500 ml/min of air | 14.6 | 143275 | 34 | 520 | 0 | 0 | 144 |
| 21.10 | Co(OAc)2 0.7 g HBr 0.8 | 200° C., 10 min | 14.7 | 145790 | 0 | 1830 | 0 | 0 | 160 |
| 24.10 | Co(OAc)2 0.7 g HBr 0.8 | 200° C., 30 min | 14.8 | 144338 | 0 | 660 | 0 | 0 | 155 |

The oxidation was slower with the ionic liquid than with NH$_4$OAc. Comparison of liquid chromatography (LC) data indicated that the purified product contained lesser amount of admixtures with ionic liquid than with NH$_4$OAc. No terephthalic acid amide was found.

In the presence of HBr, the oxidation of 4-CBA may proceed more slowly, but more selectively to produce high yield of purified terephthalic acid even after treatment for 30 min. The 4-CBA content was reduced 7 times by means of the oxidative purification.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for oxidizing crude terephthalic acid comprising:
    contacting solid crude terephthalic acid with a solvent comprising a carboxylic acid and one or more of an ionic liquid or ammonium acetate; a bromine source; a catalyst; and an oxidizing agent to produce solid purified terephthalic acid at a temperature of about 100 to about 210° C., and a pressure of about 2 to about 4.5 MPa, for a time of about 5 to about 60 min; and
    recovering the solid purified terephthalic acid.

2. The process of claim 1, wherein the temperature is about 150 to about 200° C.

3. The process of claim 1, wherein the pressure is in about 4.0 to about 4.1 MPa.

4. The process of claim 1, wherein the time is about 5 to about 45 min.

5. The process of claim 1, wherein a cation of the ionic liquid is formed from imidazoles, pyrazoles, thiazoles, isothiazoles, azathiozoles, oxothiazoles, oxazines, oxazolines, oxazaboroles, dithiozoles, triazoles, selenozoles, oxahospholes, pyrroles, boroles, furans, thiphenes, phospholes, pentazoles, indoles, indolines, oxazoles, isothirazoles, tetrazoles, benzofuran, dibenzofurans, benzothiophenes, dibenzothoiphenes, thiadiazoles, pyrdines, pyrimidines, pyrazines, pyridazines, piperazines, piperidines, morpholines, pyrans, annolines, phthalazines, quinazolines, quinoxalines, alkyl phosphonium, or combinations thereof.

6. The process of claim 1, wherein an anion of the ionic liquid is halides, borides, phosphates, arsenates, stibates, acetate, carboxylates, azolates, sulfates, acyl units, tetrafluoroborates, tosylates, imides, $CO_3^{2-}$, $NO_2^{1-}$, $NO_3^{1-}$, $SO_4^{2-}$, $PO_4^{3-}$, $(CF_3)SO_3^{1-}$, derivatives thereof, or combinations thereof.

7. The process of claim 1, wherein ionic liquid comprises dialkylimidazolium halides, dialkylimidazolium carboxylates, or dialkylimidazolium acetates.

8. The process of claim 1 wherein there are at least two ionic liquids.

9. The process of claim 1, wherein water is present in the contacting step.

10. The process of claim 1, wherein the purified terephthalic acid has less than about 1000 ppm 4-carboxybenzaldehyde.

11. The process of claim 1, wherein the purified terephthalic acid has less than about 750 ppm 4-carboxybenzaldehyde.

12. The process of claim 1, wherein the purified terephthalic acid has less than about 100 ppm 4-carboxybenzaldehyde.

13. The process of claim 1 wherein the carboxylic acid is present in a range of about 30 to about 70 wt %, the ionic liquid is present in a range of 0 to about 30 wt %, the ammonium acetate is present in a range of 0 to about 30 wt %, the bromine source is present in a range of about 0.005 to about 2 wt %, and the catalyst is present in an amount of about 0.05 to about 4 wt %, wherein the wt % is based on the total oxidation mixture.

14. A process for oxidizing crude terephthalic acid comprising:
contacting solid crude terephthalic acid with a solvent comprising acetic acid, and one or more of dialkylimidazolium halides, or ammonium acetate; a bromine source; a catalyst; and an oxidizing agent to produce solid purified terephthalic acid at a temperature of about 150 about 200° C., and a pressure of about 4.0 to about 4.1 MPa, for a time of about 5 to about 60 min; and recovering the solid purified terephthalic acid.

15. The process of claim 14, wherein the purified terephthalic acid has less than about 1000 ppm 4-carboxybenzaldehyde.

16. The process of claim 14, wherein the purified terephthalic acid has less than about 750 ppm 4-carboxybenzaldehyde.

17. The process of claim 14, wherein the purified terephthalic acid has less than about 100 ppm 4-carboxybenzaldehyde.

18. The process of claim 14 wherein there are at least two ionic liquids.

19. The process of claim 14, wherein water is present in the contacting step.

20. The process of claim 14 wherein the acetic acid is present in a range of about 30 to about 70 wt %, the dialkylimidazolium halide is present in a range of 0 to about 30 wt %, the ammonium acetate is present in a range of 0 to about 30 wt %, the bromine source is present in a range of about 0.05 to about 2 wt %, and the catalyst is present in an amount of about 0.05 to about 4 wt %, wherein the wt % is based on total oxidation mixture.

* * * * *